(12) United States Patent
Horai et al.

(10) Patent No.: US 6,888,918 B2
(45) Date of Patent: May 3, 2005

(54) SURFACE INSPECTION METHOD AND SURFACE INSPECTION APPARATUS

(75) Inventors: Izuo Horai, Odawara (JP); Kenji Aikou, Ninomiya-machi (JP); Kyoichi Mori, Oiso-machi (JP)

(73) Assignee: Hitachi High-Tech Electronics Engineering Co., Ltd., Tokyo (JP)

( * ) Notice: Subject to any disclaimer, the term of this patent is extended or adjusted under 35 U.S.C. 154(b) by 0 days.

(21) Appl. No.: 10/715,767

(22) Filed: Nov. 18, 2003

(65) Prior Publication Data

US 2004/0101099 A1 May 27, 2004

(30) Foreign Application Priority Data

Nov. 18, 2002 (JP) ..................................... P 2002-333057

(51) Int. Cl.[7] .............................................. G01B 15/06
(52) U.S. Cl. ............................. 378/58; 378/44; 356/72
(58) Field of Search ............................... 378/44–45, 50, 378/70, 86–90, 58; 356/72, 237.1–237

(56) References Cited

U.S. PATENT DOCUMENTS 6,590,645 B1 * 7/2003 Chen et al. .............. 356/237.2
6,801,595 B2 * 10/2004 Grodzins et al. ............. 378/45
6,810,105 B2 * 10/2004 Nasser-Ghodsi et al. ..... 378/44

FOREIGN PATENT DOCUMENTS

| JP | 2000-12317 | 4/2000 | ........... G01B/11/00 |
| JP | 2000-234912 | 8/2000 | ........... G01B/11/06 |
| JP | 2001-066263 | 3/2001 | ........... G01N/21/95 |
| JP | 2001-133421 | 5/2001 | ......... G01N/23/223 |

* cited by examiner

Primary Examiner—David V. Bruce
Assistant Examiner—Hoon Song
(74) Attorney, Agent, or Firm—Mayer, Fortkort & Williams, PC; Karin L. Williams, Esq.

(57) ABSTRACT

An optical inspection unit inspects a surface of an object under inspection optically. A processing unit detects defects on the surface of the object under inspection and their features according to inspection results from the optical inspection unit, detects positions of the detected defects on the surface of the object under inspection, and classifies the detected defects according to their features. The processing unit selects the defects, on which a X-ray analysis should be performed, according to predetermined conditions about the features or the classification results of the defects. Alternatively, the processing unit displays the positions and the classification results of the defects, and an operator picks the defects, on which the X-ray analysis should be performed. A X-ray inspection unit performs the X-ray analyses on the selected or picked defects.

20 Claims, 4 Drawing Sheets

- ▫ : Bump (small)
- ▫ : Bump (large)
- ◆ : Particle (small)
- ◇ : Particle (large)
- ○ : Pit (small)
- ○ : Pit (large)
- ▲ : Scratch (small)
- △ : Scratch (large)
- ● : Others

| No | Address | | Up/Down judgment | Size [μm] | Height/ Depth [μm] | Detected amounts of elements by X-ray analysis | | | Substance judgment |
|---|---|---|---|---|---|---|---|---|---|
| | X | Y | | | | A | B | C | |
| 1 | | | | | | | | | |
| 2 | | | | | | | | | |
| 3 | | | | | | | | | |
| ⋮ | | | | | | | | | |

SURFACE INSPECTION METHOD AND SURFACE INSPECTION APPARATUS

FIELD OF THE INVENTION

The present invention relates to a surface inspection method and a surface inspection apparatus for inspecting whether an object under inspection, such as a magnetic disk, a semiconductor wafer and a liquid crystal substrate, for example, has defects on its surface. It especially relates to the surface inspection method and the surface inspection apparatus, which inspect the surface of the object under inspection optically.

BACKGROUND OF THE INVENTION

A surface inspection apparatus, which inspects the surface of the object under inspection optically, a scattered light detection type or a reflected light detection type, in which the surface of the object under inspection is illuminated by a inspection light and a scattered light or a reflected light from the surface of the object under inspection is detected, is generally known (See Japanese Patent Laid-Open 2001-66263, for example). The scattered light detection type and the reflected light detection type are suitable for measuring shapes, sizes, etc. of the defects on the surface of the object under inspection.

There is also an interference phase detection type, in which a reference surface and the surface of the object under inspection are illuminated by divided inspection lights, and the interference between a reflected light from the reference surface and a reflected light from the surface of the object under inspection is detected (Japanese Patent Laid-Open 2000-121317, for example). The interference phase detection type is suitable for measuring heights, depths, etc. of the defects on the surface of the object under inspection. It is also utilized for measuring thicknesses of semiconductor wafers, etc. (Japanese Patent Laid-Open 2000-234912, for example).

In consideration of differences in the shapes, sizes, optical characters, etc. of the defects, some surface inspection apparatus adopt two or more of the above-mentioned detection methods.

In a surface inspection of a magnetic disk or its substrate, for example, there are various kinds of defects to be detected, such as particles, stains, pits, bumps, dimples, scratches, handling damages, grinds, etc. Although these various defects should be detected and discriminated during the surface inspection, the discrimination accuracy of the defects naturally has some limits when using the above-mentioned optical detection methods only.

Moreover, when foreign matters, such as the particles, stains, etc., are adhering to the surface of the object under inspection, such as the magnetic disk, a semiconductor wafer, a liquid crystal substrate, etc., it is necessary to prove substances of the foreign matters in order to manage production processes. However, it was sometimes difficult to know the substances of the foreign matters from the shapes, sizes, heights, etc., which are measured by the above-mentioned optical detection methods, and detailed analyses are separately needed.

SUMMARY OF THE INVENTION

The purpose of the present invention is to improve the discrimination accuracy of the defects during the surface inspection.

Another purpose of the present invention is to prove the substances of the foreign matters, which are adhering to the surface of the object under inspection, during the surface inspection.

A feature of the present invention is inspecting the surface of the object under inspection optically, detecting the defects on the surface of the object under inspection and their features according to inspection results, detecting positions of the detected defects on the surface of the object under inspection, classifying the detected defects according to their features, and performing X-ray analyses on the defects based on the positions of the defects and the features or classification results of the defects.

After inspecting the surface of the object under inspection optically, the X-ray analyses are performed on the defects either automatically with a program, or by directions from an operator. Since the X-ray analyses on the defects are performed based on the positions of the defects and the features or the classification results of the defects, which are detected by an optical inspection, it becomes possible to perform analysis works efficiently. It also becomes possible to determine the substances of the foreign matters, such as the particles, stains, etc., which are adhering to the surface of the object under inspection, from X-ray analysis results of the defects.

Another feature of the present invention is performing re-classifications of the defects according to the X-ray analysis results of the defects. It becomes possible to improve the discrimination accuracy of the defects by using the X-ray analysis results of the defects in addition to the features, such as the shapes, sizes, heights, etc., which are detected by the optical inspection. For example, when the X-ray analysis results differ, it becomes possible to discriminate the particles from the bumps even if the features, such as the shapes, sizes, heights, etc., which are detected by the optical inspection, are the same. Therefore, it becomes possible to classify the defects accurately by performing the re-classifications of the defects according to the X-ray analysis results of the defects.

Another feature of the present invention is that the X-ray analyses are performed on the defects, which are selected according to predetermined conditions about the features or the classification results of the defects. By programming sampling conditions of the defects and the priority for performing the X-ray analyses beforehand, the surface inspection apparatus can select the defects, on which the X-ray analysis should be performed, automatically.

Another feature of the present invention is displaying the positions and the classification results of the defects, and picking the defects, on which the X-ray analysis should be performed, among the displayed defects. The operator can pick the defects, on which the X-ray analysis should be performed, suitably based on the positions and the classification results of the displayed defects.

Another feature of the present invention is displaying the positions and the classification results of the defects, picking the defects, on which a shape analysis should be performed, among the displayed defects, reexamining the picked defects optically, performing the shape analyses on the defects according to reexamination results, and picking the defects, on which the X-ray analysis should be performed, based on shape analysis results. The operator can judge the necessity of the X-ray analyses of the defects based on the shape analysis results of the displayed defects.

Another feature of the present invention is displaying the positions and the classification results of the defects, picking the defects, on which an observation using an optical microscope should be performed, among the displayed defects, observing the picked defects using the optical microscope, and picking the defects, on which the X-ray analysis should be performed, based on observation results. The operator can judge the necessity of the X-ray analyses of the defects based on the observation results using the optical microscope.

DETAILED DESCRIPTION OF PREFERRED EMBODIMENTS

Figure 1:
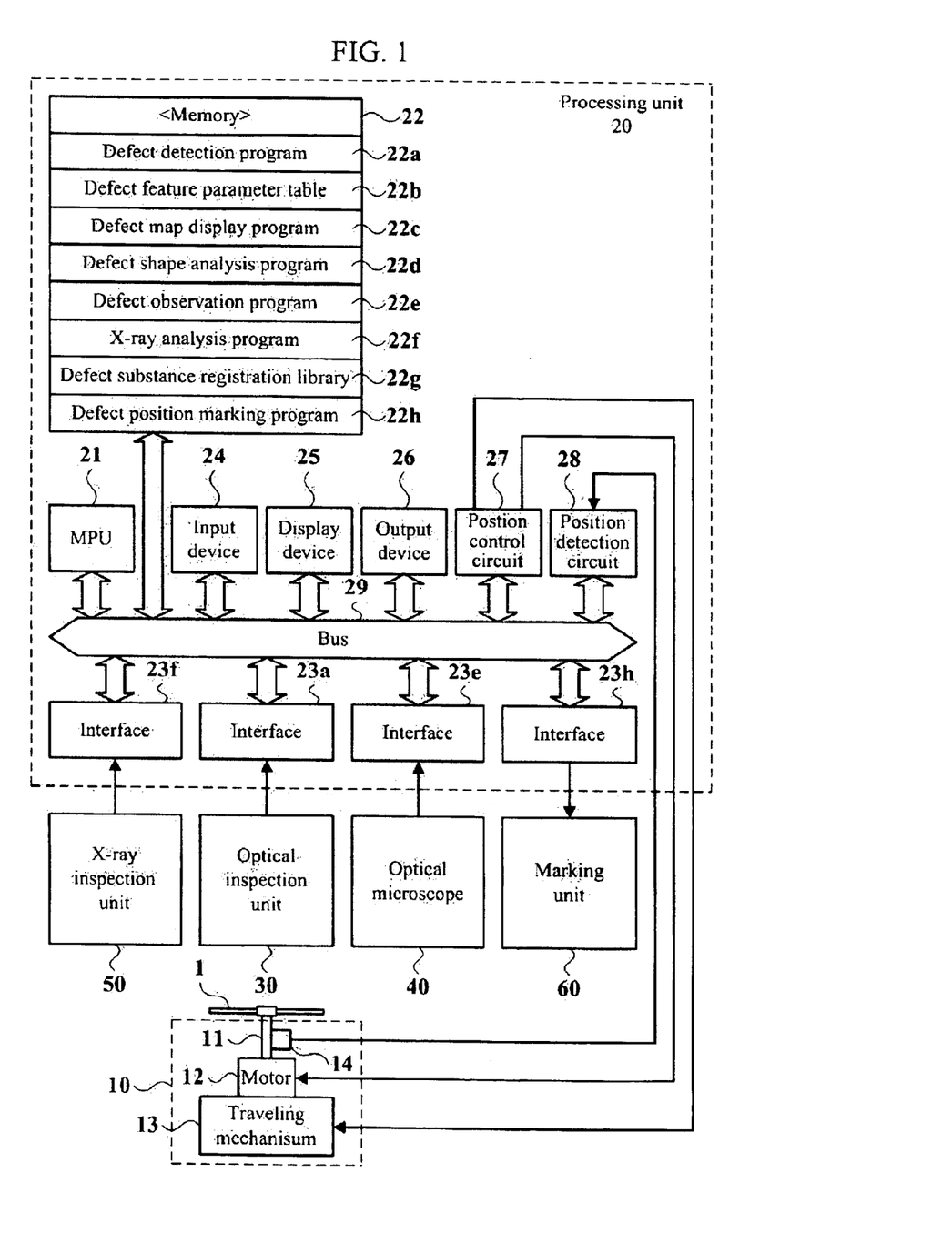
FIG. 1 is a schematic view showing an example of the surface inspection apparatus according to the present invention.

Further details are explained below with the help of examples illustrated in the attached drawings. FIG. 1 is a schematic view showing an example of the surface inspection apparatus according to the present invention. This example shows the surface inspection apparatus, which inspects defects on a surface of a magnetic disk. The surface inspection apparatus comprises an inspection stage 10, a processing unit 20, an optical inspection unit 30, an optical microscope 40, a X-ray inspection unit 50 and a marking unit 60.

The inspection stage 10 comprises a spindle 11, a motor 12, a traveling mechanism 13 and a position detector 14. In a loader portion that is not illustrated, a magnetic disk 1, which is an object under inspection, is mounted on the top of the spindle 11 using a handling mechanism that is not illustrated so that the surface under inspection turns upwards. And as shown in FIG. 1, the magnetic disk 1 is placed under the optical inspection unit 30 by the traveling mechanism 13. Under the optical inspection unit 30, the spindle 11, which is driven by the motor 12, rotates the magnetic disk 1, and the traveling mechanism 13 moves the magnetic disk 1 in its radius direction. Because of these rotations and movements, an inspection spotlight from the optical inspection unit 30 scans the surface of the magnetic disk 1 spirally. Instead of the traveling mechanism 13, a scan on the surface of the magnetic disk 1 may be carried out by moving the inspection spotlight from the optical inspection unit 30 in a radius direction of the magnetic disk 1.

The optical inspection unit 30 is the same as that of conventional surface inspection apparatuses. It comprises optical systems of the scattered light detection type and the reflected light detection type, which are described in Japanese Patent Laid-Open 2001-66263, for example, or an optical system of the interference phase detection type, which is described in Japanese Patent Laid-Open 2000-1213 17, for example, or both.

The processing unit 20 comprises a MPU 21, a memory 22, interfaces 23a, 23e, 23f, 23h, an input device 24, a display device 25, an output device 26, a position control circuit 27, a position detection circuit 28 and a bus 29. The MPU 21 controls the memory 22, the interfaces 23a, 23e, 23f, 23h, the input device 24, the display devise 25, the output device 26, the position control circuit 27 and the position detection circuit 28 through the bus 29.

Figure 2:
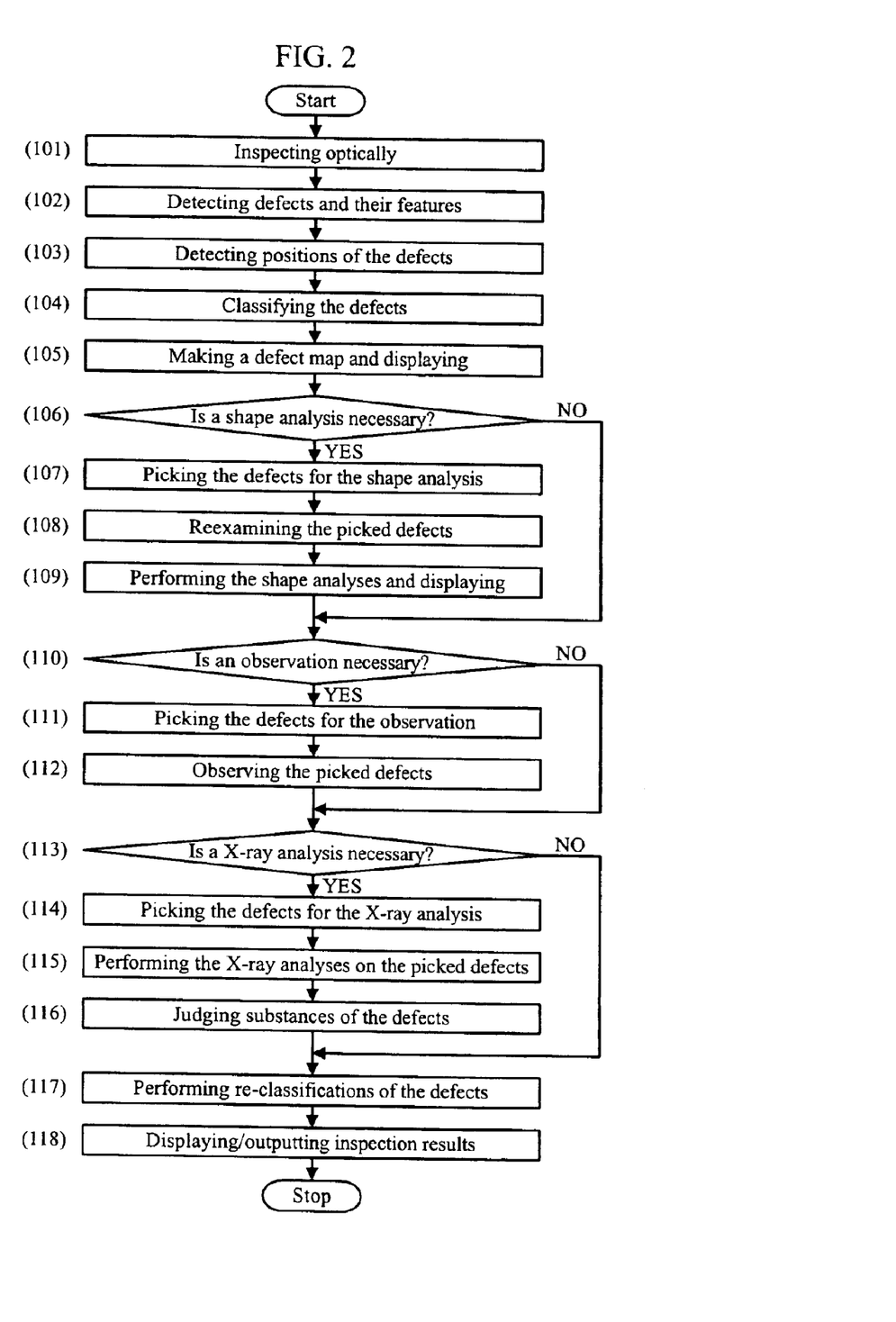
FIG. 2 is a flowchart showing an example of the surface inspection method according to the present invention.

FIG. 2 is a flowchart showing an example of the surface inspection method according to the present invention. This example shows a case where an operator of the surface inspection apparatus picks the defects, on which a X-ray analysis should be performed, using the input device 24.

First, the MPU 21 runs a defect detection program 22a, which is stored in the memory 22. Under the control of the MPU 21, the position control circuit 27 drives the motor 12 and the traveling mechanism 13 so that the inspection spotlight from the optical inspection unit 30 scans the surface of the magnetic disk 1. The optical inspection unit 30 inspects the surface of the magnetic disk 1 optically (Step 101), and outputs inspection results to the interface 23a. The position detector 14 consists of a rotary encoder, for example. It detects a reference position and rotations of the magnetic disk 1 from rotations of the spindle 11, and outputs detection signals to the position detection circuit 28.

The MPU 21 detects the defects on the surface of the magnetic disk 1 and their features according to the inspection results, which are detected by the optical inspection unit 30 and input through the interface 23a (Step 102). The detected features of the defects may be the unevenness (up or down) of the defects, their sizes, and their heights or depths, for example. Under the control of the MPU 21, the position detection circuit 28 detects positions of the detected defects on the surface of the magnetic disk 1 from the detection signals of the position detector 14 (Step 103). The detected positions of the defects may be X coordinates and Y coordinates from the reference position on the surface of the magnetic disk 1, for example. Under the control of the MPU 21, the memory 22 relates the feature data of the detected defects to the coordinate position data of the defects, and memorizes them.

Next, the MPU 21 classifies the detected defects according to their features by comparing the feature data of the detected defects with the data of a defect feature parameter table 22b, which is stored in the memory 22 (Step 104). Classifications of the defects may be kinds of the defects, such as a bump, particle, pit, scratch, etc., and differences of their sizes, for example. Under the control of the MPU 21, the memory 22 relates the classification result data of the defects to the coordinate position data of the defects, and memorizes them.

After inspections by the optical inspection unit 30 and above-mentioned processes by the processing unit 20 are completed as to the whole surface of the magnetic disk 1, the MPU 21 runs a defect map display program 22c, which is stored in the memory 22. The MPU 21 makes a defect map from the coordinate position data of the defects and the classification result data of the defects, which are memorized in the memory 22, and displays it on a display device 25 (Step 105).

Figure 3:
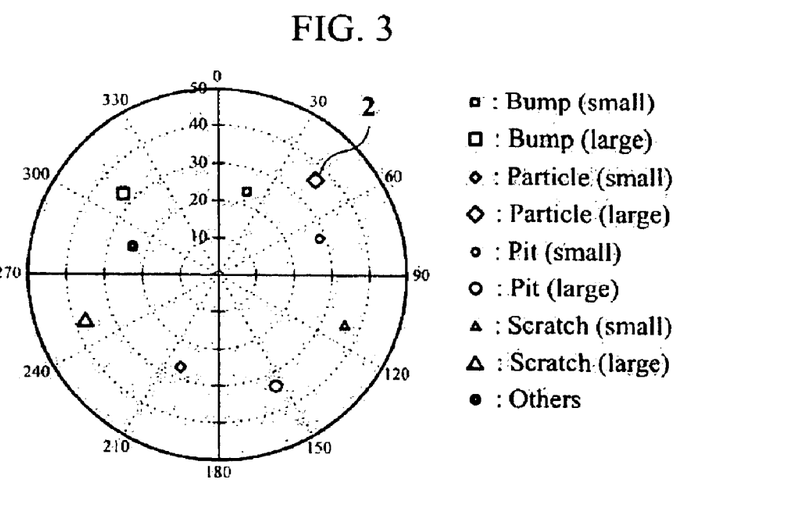
FIG. 3 shows an example of a defect map.

FIG. 3 shows an example of the defect map. The defect map symbolizes the detected defects with marks according to the classification results, and indicates the positions of the defects on the surface of the magnetic disk by positions of the marks on the map. Although the detected defects are classified and displayed using nine marks according to differences in the kinds and the sizes in the example shown in FIG. 3, the kinds of the defects and the differences in the sizes are not restricted to these. Also the marks, which are used for the defect map, are not restricted to those of the example shown in FIG. 3, and various marks may be used including color differences.

Then the operator looks at the defect map displayed on the display device 25, and judges whether a shape analysis is necessary on the individual defect (Step 106). When the operator decides that the shape analysis is necessary, he/she picks the defects, on which the shape analysis should be performed, among the displayed defects using the input device 24 (Step 107).

When the defects, on which the shape analysis should be performed, are picked, the MPU 21 runs a defect shape analysis program 22d, which is stored in the memory 22. Under the control of the MPU 21, the position control circuit 27 drives the motor 12 and the traveling mechanism 13 for rotating and moving the magnetic disk 1 based on the coordinate position data of the picked defects, which are memorized in the memory 22, so that the picked defects are illuminated by the inspection spotlight from the optical inspection unit 30. By this, the optical inspection unit 30 reexamines the picked defects on the surface of the magnetic disk 1 in detail (Step 108), and outputs reexamination results to the interface 23a.

The MPU 21 performs the shape analyses on the picked defects according to the reexamination results, which are detected by the optical inspection unit 30 and input through the interface 23a, and displays shape analysis results on the display device 25 (Step 109). The displayed shape analysis results may be anything, from which the operator can judge the shapes of the defects visually, such as 3-dimensional images, contour maps, sectional shapes, for example.

Then the operator looks at the defect map or the shape analysis results of the defects displayed on the display device 25, and judges whether an observation using the optical microscope is necessary on the individual defect (Step 110). When the operator decides that the observation using the optical microscope is necessary, he/she picks the defects, on which the observation using the optical microscope should be performed, among the displayed defects using the input device 24 (Step 111).

When the defects, on which the observation using the optical microscope should be performed, are picked, the MPU 21 runs a defect observation program 22e, which is stored in the memory 22. Under the control of the MPU 21, the position control circuit 27 drives the traveling mechanism 13 so that the magnetic disk 1 is placed under the optical microscope 40. Instead of the traveling mechanism 13, the magnetic disk 1 may be placed under the optical microscope 40 by mounting it on another inspection stage, which is located under the optical microscope 40, using a handling mechanism that is not illustrated.

Next, under the control of the MPU 21, the position control circuit 27 drives the motor 12 and the traveling mechanism 13 for rotating and moving the magnetic disk 1 based on the coordinate position data of the picked defects, which are memorized in the memory 22, so that the optical microscope 40 detects picture images of the picked defects. Then under the control of the MPU 21, the position control circuit 27 drives the traveling mechanism 13 upward/downward and carries out an auto-focus based on the height/depth data of the picked defects, which are memorized in the memory 22, so that the optical microscope 40 focuses on surfaces of the picked defects. By this, the optical microscope 40 detects the picture images of the picked defects on the surface of the magnetic disk 1, and outputs them to the interface 23e.

The MPU 21 displays the picture images, which are detected by the optical microscope 40 and input through the interface 23e, on the display device 25. The operator observes the picture images of the picked defects displayed on the display device 25 (Step 112).

After looking at the defect map or the shape analysis results of the defects displayed on the display device 25, or based on observation results of the defects using the optical microscope, the operator judges whether a X-ray analysis is necessary on the individual defect (Step 113). When the operator decides that the X-ray analysis is necessary, he/she picks the defects, on which the X-ray analysis should be performed, among the displayed defects using the input device 24 (Step 114). On the defect map shown in FIG. 3, here assume that a particle with a numeral "2" is picked.

When the defects, on which the X-ray analysis should be performed, are picked, the MPU 21 runs a X-ray analysis program 22f, which is stored in the memory 22. Under the control of the MPU 21, the position control circuit 27 drives the traveling mechanism 13 so that the magnetic disk 1 is placed under the X-ray inspection unit 50. Instead of the traveling mechanism 13, the magnetic disk 1 may be placed under the X-ray inspection unit 50 by mounting it on another inspection stage, which is located under the X-ray inspection unit 50, using a handling mechanism that is not illustrated.

Figure 4:
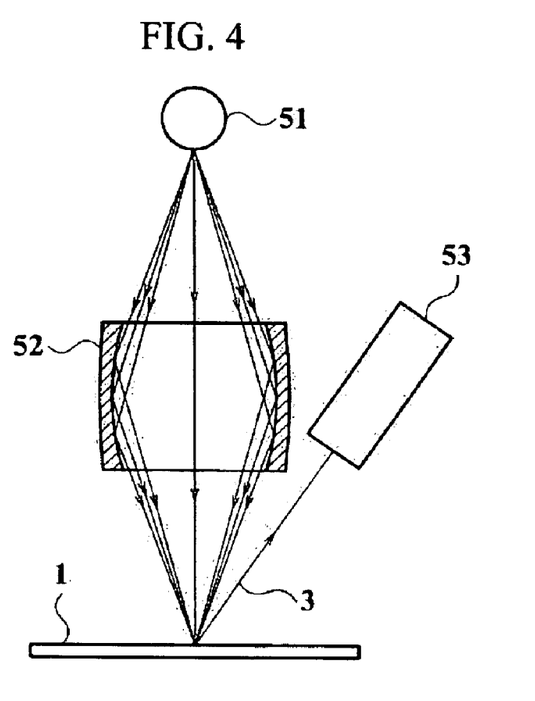
FIG. 4 is a schematic view showing an example of a X-ray inspection unit in the surface inspection apparatus according to the present invention.

FIG. 4 is a schematic view showing an example of the X-ray inspection unit in the surface inspection apparatus according to the present invention. The X-ray inspection unit 50 comprises a X-ray tube 51, a spectroscopic device 52 and a X-ray detector 53. The X-ray tube 51 generates primary X-rays, which are radiated to the surface of the magnetic disk 1. The spectroscopic device 52 has a barrel-type cylindrical shape, whose center portion swells as the section is shown in FIG. 4. It carries out the Bragg reflection only on the primary X-rays, which come into its inner surface with a predetermined incidence angle, and directs them to the surface of the magnetic disk 1. When the primary X-rays are radiated, atoms on the surface of the magnetic disk 1 are excited, and fluorescent X-rays 3 are generated. The X-ray detector 53 detects the fluorescent X-rays 3, which are generated from the surface of the magnetic disk 1. A spectroscopic apparatus and a X-ray analysis apparatus, such as that shown in Japanese Patent Laid-Open 2001-133421 is known.

Under the control of the MPU 21, the position control circuit 27 drives the motor 12 and the traveling mechanism 13 for rotating and moving the magnetic disk 1 based on the coordinate position data of the picked defects, which are memorized in the memory 22, so that the primary X-rays from the X-ray inspection unit 50 are radiated to the picked defects. By this, the X-ray inspection unit 50 performs the X-ray analyses on the picked defects on the surface of the magnetic disk 1 (Step 115), and outputs X-ray analysis results to the interface 23f.

Figure 5:
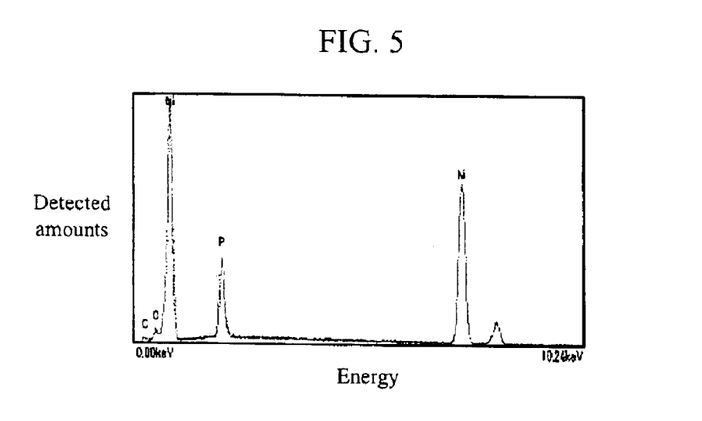
FIG. 5 shows an example of X-ray analysis results.

FIG. 5 shows an example of the X-ray analysis results. This shows the example, in which particles containing carbon (C) and oxygen (O) exist on the surface of the magnetic disk 1, whose base material comprises nickel-phosphorus (Ni-P). In FIG. 5, a horizontal axis shows the energy of elements, and a vertical axis shows detected amounts. Portions indicated by "C" and "O" in FIG. 5 show the detected amounts of carbon (C) and oxygen (O) respectively.

The MPU 21 judges substances of the picked defects by comparing the X-ray analysis result data, which are detected by the X-ray inspection unit 50 and input through the interface 23f, with the spectrum data of substances registered in a defect substance registration library 22g, which is stored in the memory 22 (Step 116). In consideration of materials constituting the object under inspection and foreign matters, which could be mixed during manufacturing processes, etc., the defect substance registration library 22g registers the spectrum data of substances, which have a possibility of detections by the X-ray analysis, beforehand. Substance judgment results of the defects may be kinds of organic or inorganic matters, kinds of metals, kinds of magnetic materials, kinds of semiconductors, kinds of amorphous carbons and water stains, for example. Under the control of the MPU 21, the memory 22 relates the X-ray analysis result data of the defects and the substance judgment result data of the defects to the coordinate position data of the defects, and memorizes them.

Next, the MPU 21 performs re-classifications of the defects based on the substance judgment result data of the defects (Step 117). About the particle with the numeral "2" on the defect map shown in FIG. 3, for example, it will be re-classified not as a particle but as a bump if the substance judgment result is the same as that of the base material of the magnetic disk 1. On the other hand, it will be re-classified as a particle again if the substance judgment result is different from that of the base material of the magnetic disk 1. Furthermore, the particle may be finely re-classified according to the kind of the substance. Under the control of the MPU 21, the memory 22 relates the re-classification result data of the defects to the coordinate position data of the defects, and memorizes them.

Finally, based on the coordinate position data of the defects, the feature data of the defects, the X-ray analysis result data of the defects and the substance judgment result data of the defects, which are all memorized in the memory 22, the MPU 21 displays inspection results on the display 25 device, or outputs them to the output device 26 (Step 118).

Figure 6:
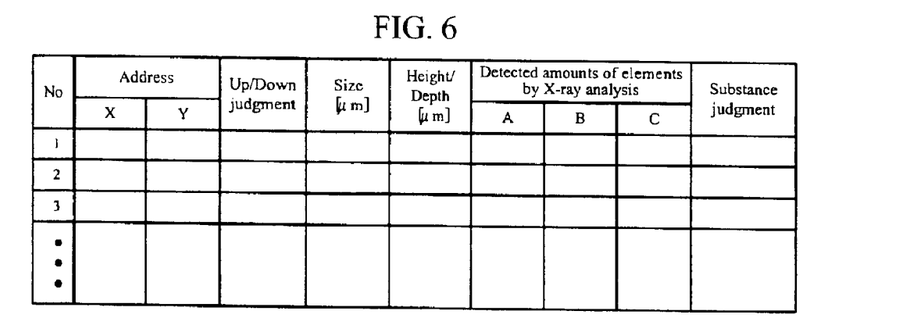
FIG. 6 shows an example of inspection results output from the inspection apparatus.

FIG. 6 shows an example of the inspection results output from the surface inspection apparatus. Numbers in a "No" column are serial numbers for distinguishing each defect. The X coordinates and the Y coordinates of the defect positions on the magnetic disk 1 are displayed in a "X" column and a "Y" column of an "Address". The unevenness (up or down) of the defects is displayed in an "Up/Down judgment" column. The sizes of the defects are displayed in a "Size" column, and the heights or the depths of the defects are displayed in a "Height/Depth" column. The detected amounts of elements A, B and C (A, B and C indicate an arbitrary elements respectively) by the X-ray analysis are displayed in an "A" column, "B" column and "C" column of "Detected amounts of elements by X-ray analysis". The substance judgment results of the defects are displayed in a "Substance judgment" column. The inspection results displayed or output are not restricted to this example. They may show the features of the defects, the classification or re-classification results of the defects, the X-ray analysis results of the defect, etc. more simply or in detail.

According to the example shown in FIG. 2, the operator can pick the defects, on which the X-ray analysis should be performed, suitably from the defect map displayed on the display device. Furthermore, the operator can judge the necessity of the X-ray analyses of the defects based on the shape analysis results of the defects displayed on the display device, or based on the observation results of the defects using the optical microscope. However, the shape analyses of the defects and the observations of the defects using the optical microscope are not mandatory, either of them may be performed, or both may be neglected. Moreover, the shape analyses of the defects may be performed after the observations of the defects using the optical microscope.

Although the example shown in FIG. 2 is the case where the operator of the surface inspection apparatus picks the defects, on which the X-ray analysis should be performed, the surface inspection apparatus can select the defects, on which the X-ray analysis should be performed, automatically. In this case, a program for selecting the defects, on which the X-ray analysis should be performed, is added to the memory 22. The MPU 21 runs the added program and selects the defects, on which the X-ray analysis should be performed. And the X-ray analyses are performed on the selected defects just like the case where the operator picks the defects.

The program for selecting the defects, on which the X-ray analysis should be performed, includes sampling conditions of the defects, the priority for performing the X-ray analyses, etc. For example, the surface of the magnetic disk 1 is divided into some blocks of a predetermined area. The blocks, in which the defect density (the number of the defects detected in each block) is a predetermined amount or more, are selected in order of the defect density. And a defect having the maximum size in the selected block or defects having a predetermined size or more are sampled from the selected block. The sampling conditions of the defects and the priority for performing the X-ray analyses are not restricted to these. They may be determined suitably, such as in order of the size among defects having a predetermined size or more, or in a predetermined classification order among defects classified in specific kinds.

The inspection by the surface inspection apparatus shown FIG. 1 is over. Then after looking at the defect map or the shape analysis results of the defects displayed on the display device 25, or based on the observation results of the defects using the optical microscope, or after looking at the inspection results displayed on the display device 25 or output from the output device 26, the operator can judge whether the marking of the defect position on the surface of the magnetic disk 1 is necessary on the individual defect. When the operator decides that the marking is necessary, he/she picks the defects, about which the marking should be performed, among the displayed defects using the input device 24.

When the defects, for which the marking should be performed, are picked, the MPU 21 runs a defect position marking program 22h, which is stored in the memory 22. Under the control of the MPU 21, the position control circuit 27 drives the traveling mechanism 13 so that the magnetic disk 1 is placed under the marking unit 60. Instead of the traveling mechanism 13, the magnetic disk 1 may be placed under the marking unit 60 by mounting it on another inspection stage, which is located under the marking unit 60, using a handling mechanism that is not illustrated.

Next, among the coordinate position data and the classification or re-classification results data of the defects, which are memorized in the memory 22, the MPU 21 outputs the coordinate position data and the classification or re-classification results data of the picked defects to the marking unit 60 through the interface 23h. The marking unit 60 puts marks, which indicate the positions and the classification or re-classification results of the picked defects, on the surface of the magnetic disk 1 based on the input coordinate position data and the input classification or re-classification results data of the defects. The marks put on the surface of the magnetic disk 1 are utilized when performing further analyses in detail using a scanning electron microscope (SEM) or a atomic force microscope (AFM), for example.

Moreover, the surface inspection apparatus can select the defects, for which the marking should be performed, automatically. In this case, a program for selecting the defects, about which the marking should be performed, is added to the memory 22. The MPU 21 runs the added program and selects the defects, for which the marking should be performed, the marking is performed for the selected defects as in the case in which the operator picks the defects.

Although the above-mentioned example explains a case of performing an X-ray analysis on a particle, which is adhering to the surface of the magnetic disk 1, substances of other foreign matters, such as stains, etc., can be also proved by performing the X-ray analysis. Moreover, when layers formed on the surface of the magnetic disk, such as a magnetic film, a protective film, etc., have a damage, such as scratches etc., it is possible to judge which layer is exposed by performing the X-ray analysis.

The present invention is not restricted to the magnetic disk but is also applicable in inspecting defects on surfaces of various things, such as a semiconductor wafer, a liquid crystal substrate, etc.

According to the present invention, it becomes possible to improve the discrimination accuracy of the defects using the X-ray analysis results of the defects. Therefore, it becomes possible to classify the defects accurately by performing the re-classifications of the defects according to the X-ray analysis results of the defects.

Since the X-ray analyses on the defects are performed based on the positions of the defects and the features or the classification results of the defects, which are detected by the optical inspection, it becomes possible to perform analysis works efficiently.

Moreover, it becomes possible to prove the substances of the foreign matters, such as the particles, stains, etc., which are adhering to the surface of the object under inspection, from the X-ray analysis results of the defects. By this, it becomes possible to find out sources of the foreign matters, which have adhered to the surface of the magnetic disk, the semiconductor wafer, the liquid crystal substrate, etc. during production processes, and quick pollution preventive measures become possible.

What is claimed is:

1. A surface inspection method comprising the steps of:
   inspecting a surface of an object under inspection optically,
   detecting defects on the surface of the object under inspection and their features according to results of said inspecting step,
   detecting positions of the detected defects on the surface of the object under inspection, classifying the detected defects according to their features, and
   performing X-ray analyses on the defects based on the positions of the defects and the features or classification results of the defects.

2. The surface inspection method according to claim 1 further comprising the step of:
   performing re-classifications of the defects according to X-ray analysis results of the defects.

3. The surface inspection method according to claim 1, wherein the X-ray analyses are performed on the defects, selected according to predetermined conditions about the features or the classification results of the defects.

4. The surface inspection method according to claim 3 further comprising the step of:
   performing re-classifications of the defects according to X-ray analysis results of the defects.

5. The surface inspection method according to claim 1 further comprising the steps of:
   displaying the positions and the classification results of the defects, and picking the defects, on which the X-ray analysis should be performed, among the displayed defects.

6. The surface inspection method according to claim 5 further comprising the step of:
   performing re-classifications of the defects according to X-ray analysis results of the defects.

7. The surface inspection method according to claim 1 further comprising the steps of:
   displaying the positions and the classification results of the defects,
   picking the defects, on which a shape analysis should be performed, among the displayed defects,
   reexamining the picked defects optically,
   performing the shape analyses on the defects according to reexamination results, and picking the defects, on which the X-ray analysis should be performed, based on shape analysis results.

8. The surface inspection method according to claim 7 further comprising the step of:
   performing re-classifications of the defects according to X-ray analysis results of the defects.

9. The surface inspection method according to claim 1 further comprising the steps of:
   displaying the positions and the classification results of the defects,
   picking the defects, on which an observation using an optical microscope should be performed, among the displayed defects,
   observing the picked defects using the optical microscope, and
   picking the defects, on which the X-ray analysis should be performed, based on observation results.

10. The surface inspection method according to claim 9 further comprising the step of:
    performing re-classifications of the defects according to X-ray analysis results of the defects.

11. A surface inspection apparatus comprising: an optical inspection means for inspecting a surface of an object under inspection optically,
    a processing means for detecting defects on the surface of the object under inspection and their features according to inspection results from said optical inspection means, for detecting positions of the detected defects on the surface of the object under inspection, for classifying the detected defects according to their features, and for selecting or picking the defects, on which a X-ray analysis should be performed, and
    a X-ray inspection means for performing the X-ray analyses on the defects selected or picked by said processing means.

12. The surface inspection apparatus according to claim 11, wherein said processing means performs re-classifications of the defects according to X-ray analysis results of the defects from said X-ray inspection means.

13. The surface inspection apparatus according to claim 11, wherein said processing means selects the defects, on which the X-ray analysis should be performed, according to predetermined conditions about the features or the classification results of the defects.

14. The surface inspection apparatus according to claim 13, wherein said processing means performs re-classifications of the defects according to X-ray analysis results of the defects from said X-ray inspection means.

15. The surface inspection apparatus according to claim 11, wherein said processing means has a display device, which displays the positions and the classification results of the defects, and an input device for picking the defects, on which the X-ray analysis should be performed, among the defects displayed by said display device.

16. The surface inspection apparatus according to claim 15, wherein said processing means performs re-classifications of the defects according to X-ray analysis results of the defects from said X-ray inspection means.

17. The surface inspection apparatus according to claim 11, wherein said processing means has a display device, which displays the positions and the classification results of the defects, and an input device for picking the defects, on which a shape analysis should be performed, among the defects displayed by said display device, said optical inspection means reexamines the defects, which are picked by said input device, optically, and said processing means performs the shape analyses on the defects according to reexamination results from said optical inspection means and displays shape analysis results on said display device.

18. The surface inspection apparatus according to claim 17, wherein said processing means performs re-classifications of the defects according to X-ray analysis results of the defects from said X-ray inspection means.

19. The surface inspection apparatus according to claim 11 further comprising an optical microscope, wherein said processing means has a display device, which displays the positions and the classification results of the defects, and an input device for picking the defects, on which an observation using said optical microscope should be performed, among the defects displayed by said display device.

20. The surface inspection apparatus according to claim 19, wherein said processing means performs re-classifications of the defects according to X-ray analysis results of the defects from said X-ray inspection means.

* * * * *

UNITED STATES PATENT AND TRADEMARK OFFICE
CERTIFICATE OF CORRECTION

PATENT NO. : 6,888,918 B2 Page 1 of 1
APPLICATION NO. : 10/715767
DATED : May 3, 2005
INVENTOR(S) : Izuo Horai et al.

It is certified that error appears in the above-identified patent and that said Letters Patent is hereby corrected as shown below:

Title Page, Item (57) Abstract, line 8, after "which", change "a" to --an--.

Title Page, Item (57) Abstract, line 14, after "formed.", change "A" to --An--.

Col. 1, line 21, change first word "a" to --an--.

Col. 1, line 58, after "it", change "was" to --is--.

Col. 3, line 18, after "of", change "a" to --an--.

Col. 3, line 35, after "40,", change "a" to --an--.

Col. 3, line 64, after "comprises", change "a" to --an--.

Col. 4, line 2, after "display", change "devise" to --device--.

Col. 4, line 8, after "which", change "a" to --an--.

Col. 6, line 7, after "whether", change "a" to --an--.

Signed and Sealed this

Eighth Day of May, 2007

JON W. DUDAS
*Director of the United States Patent and Trademark Office*